United States Patent
Peter et al.

(10) Patent No.: US 6,211,390 B1
(45) Date of Patent: Apr. 3, 2001

(54) METHOD FOR PRODUCING FATTY ACID ESTERS

(76) Inventors: Siegfried Peter, Lindenweg 3, D-91080 Uttenreuth-Weiher; Ruth Ganswindt, Bahnhofstr. 11, D-63571 Gelnhausen-Haller; Eckhard Weidner, Am Dorfweiher 9, D-91056 Erlangen, all of (DE)

( * ) Notice: Subject to any disclaimer, the term of this patent is extended or adjusted under 35 U.S.C. 154(b) by 0 days.

(21) Appl. No.: 09/269,090
(22) PCT Filed: Sep. 11, 1997
(86) PCT No.: PCT/EP97/04978
§ 371 Date: Dec. 3, 1999
§ 102(e) Date: Dec. 3, 1999
(87) PCT Pub. No.: WO98/12169
PCT Pub. Date: Mar. 26, 1998

(30) Foreign Application Priority Data
Sep. 19, 1996 (DE) .............................................. 196 38 460

(51) Int. Cl.$^7$ ...................................................... C07C 51/00
(52) U.S. Cl. ............................................ 554/170; 554/169
(58) Field of Search ..................................... 554/170, 169

(56) References Cited

U.S. PATENT DOCUMENTS 2,271,619 2/1942 Bradshaw et al. .
2,360,844 10/1944 Bradshaw et al. .

OTHER PUBLICATIONS

Wright et al., 1994, Oil and Soap, 21(5):145–148.
Toyama et al., 1933, J. Soc. Chem. Ind. Japan, 36:230–232B.
von Feuge et al., 1949, J. Am. Oil Chem. Soc. 26:97–102.

*Primary Examiner*—Deborah Carr
(74) *Attorney, Agent, or Firm*—Klauber & Jackson

(57) ABSTRACT

The invention concerns a method for producing fatty acid esters from fatty acid triglyceride and in particular from animal or vegetable fats and oils by transesterification with a monovalent low-molecular weight alcohol in the presence of a homogeneous or heterogeneous catalyst. In accordance with the invention, the formed fatty acid ester is extracted from the reaction mixture by means of a near-critical extractant. In this way fatty acid esters are obtained at high yield and excellent purity. As the extractant preferably a low pressure gas having a reduced temperature at 20° C. of about 0.7, preferably of equal to or greater than 0.7, is employed. Preferred extractants are carbon dioxide, propane, butane, dimethyl ether, ethyl acetate or mixtures thereof.

27 Claims, 1 Drawing Sheet

METHOD FOR PRODUCING FATTY ACID ESTERS

Figure 1:
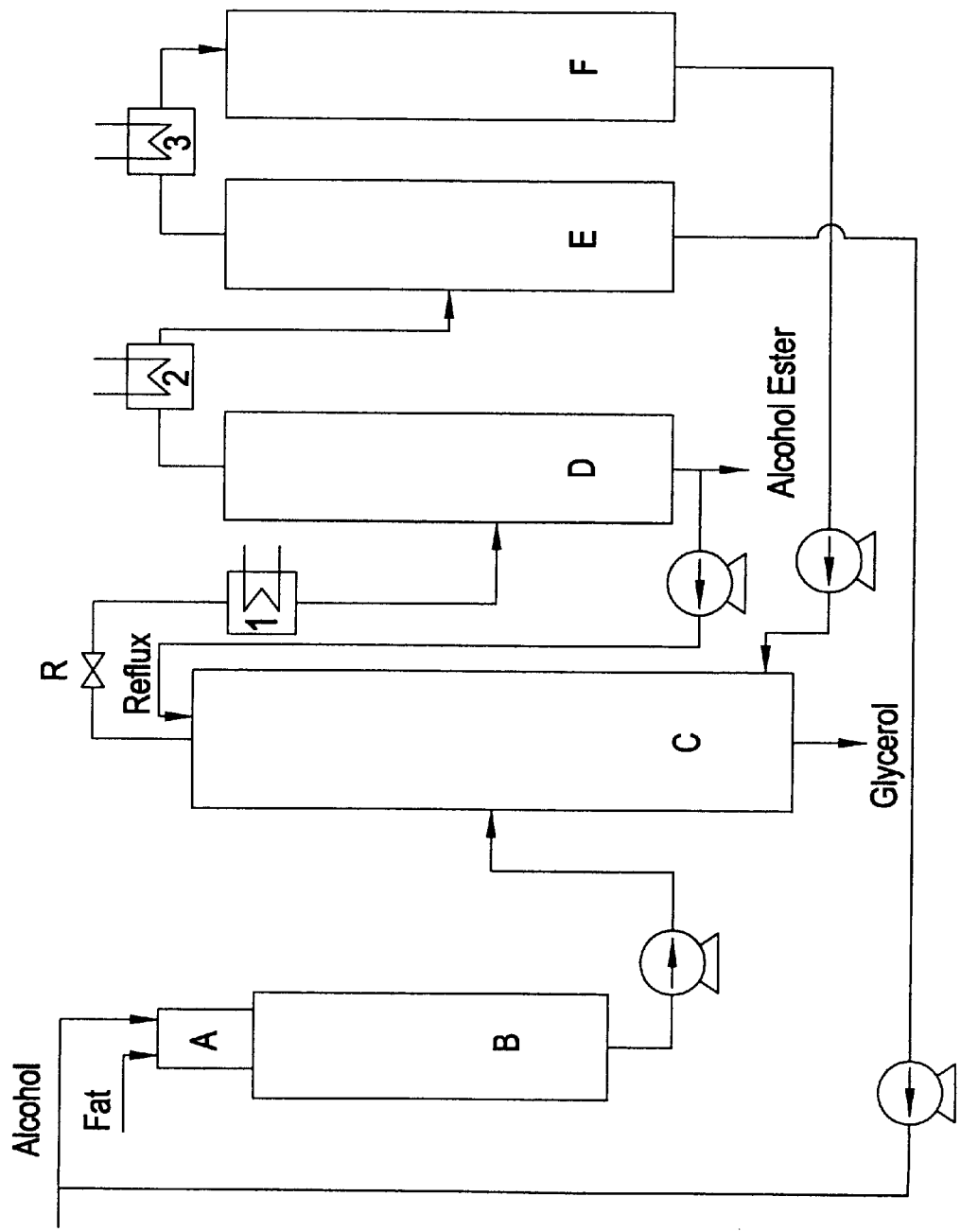

The invention concerns a method for producing fatty acid esters and in particular a method wherein fatty acid esters are obtained by transesterification of fats and oils of animal or vegetable origin.

The production of alkyl esters and in particular of methyl esters by alcoholysis of fats and oils has recently been the subject of a lively discussion with a view to the production of diesel fuels from renewable raw materials.

The glycerol component of fats and oils can, even at low temperatures, be substituted with low-molecular weight monovalent alcohols. Alcoholysis is catalysed by acids or alkalis. In technology, the Bradshaw method is frequently employed for the transesterification of fats with methanol (U.S. Pat. Nos. 2,271,619 and 2,360,844). Herein the fat which should not have an acid number in excess of 1.5 is stirred briefly at 80° C. with excess methanol in the presence of 0.1 to 0.5% sodium hydroxide. When left to rest, the glycerol separates out practically free from water at the bottom of the vessel.

The method is remarkable not only with respect to the production of methyl esters or ethyl esters directly from the fat, without an intermediate hydrolysis step, but also because of the lower reaction temperature and because special corrosion resistant equipment is not required.

If methanol is used, the reaction unfolds along the following pattern, wherein R represents a fatty acid radical:

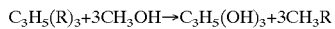

$C_3H_5(R)_3 + 3CH_3OH \rightarrow C_3H_5(OH)_3 + 3CH_3R$

The reaction is carried out in an open tank which may consist of common carbon steel. The fat must be dry, clean and above all neutral. It is heated to approx. 80° C., and commercially available, water-free methanol (99.7%) having 0.1 to 0.5% sodium hydroxide or potassium hydroxide dissolved in it is added. An amount of alcohol corresponding to about 1.6 times the theoretically required amount is recommended. The alcohol can, however, be reduced to about 1.2 times the theoretical amount if the process is performed in three steps. An amount in excess of 1.75 times the theoretical amount does not accelerate the reaction and hampers subsequent removal of the glycerol by gravity.

After adding the alcohol, the mixture is stirred for several minutes and then left to rest. The glycerol starts to separate out fairly immediately. As it is practically free from water and much heavier than the other liquids, it readily settles to form a layer at the tank bottom. Reaction of the oil into methyl ester is usually 98% complete after one hour.

The bottom layer contains not less than 90% of the glycerol originally present in the fat. The top layer is comprised of methyl esters, the major portions of the unreacted alcohol and alkali, the remaining glycerol, and a very small proportion of soap. These various impurities are removed from the esters by repeated washing with small amounts of warm water.

In the Bradshaw method the obtained methyl esters are utilized in a continuous process for producing water-free soap. The esters are readily saponified by sodium hydroxide or potassium hydroxide at a low temperature, and the highly volatile methanol is liberated and recovered for reusing.

The described method should, however, also be suited for producing monoesters for fractionation and thus custom-made fats and oils. The methyl esters and ethyl esters of the fatty acids are liquid and relatively stable, not corrosive and low-boiling, and are therefore frequently preferred to the free acids, in particular when fractionating must be carried out at elevated temperatures as is the case in distillation.

Transesterification of peanut oil with ethanol was studied in detail by Feuge and Gros, J. Am. Oil Chem. Soc. 26 (1949) 97–102. They found that the optimum temperature for the reaction is in the vicinity of 50° C. At this temperature a higher glycerol yield was obtained than at 30° C. or 70° C.

The described alcoholysis of triglycerides generally does, however, not only yield in free glycerol and monoester, but moreover monoglycerides and diglycerides and partial esters of the respective alcohol are formed.

Toyama et al. (Y. Toyama, T. Tsuchiya and T. Ishikawa, J. Soc. Chem. Ind. Japan, 36 (1933) 230–232B) demonstrated e.g. that in the presence of sodium hydroxide, equilibrium between methanol or ethanol and fats is reached within two hours at room temperature. In order to have the reaction continue until complete transformation of the fat into the monoester, it is necessary in this method to separate the released glycerol from the reaction mixture.

In a study by Wright et al. (H. J. Wright, J. B. Segur, H. V. Clark, S. K. Coburn, E. E. Langdon and R. N. DuPuis, Oil & Soap, 21 (1944) 145–148) the precise conditions for the alcoholysis of fats with methanol and ethanol are investigated in detail. It furthermore reports about experiments on alcoholysis with other monohydroxy alcohols. It is pointed out that the above described alcoholysis, catalysed by alkali, is only entirely successful if the fat is practically free from free fatty acids and if the reaction mixture is free from water. Where one of these conditions is not met, saponification ensues, resulting in a loss of alkalinity and formation of a gel structure which prevents or slows down separation and settling of the glycerol. Difficulties occur in ethanolysis if the content of free fatty acids in the fat is in excess of about 0.5%. When 30 parts ethanol, 100 parts cottonseed oil and 0.5% sodium hydroxide are made to react, the glycerol yield is considerably reduced by 0.3% water in the reaction mixture. The effect of moisture can, however, be partly compensated by the addition of further alkali and/or alcohol. The water tolerance of the above mixture is raised to 0.5 to 0.6% by doubling the catalyst content or by raising the quantity of alcohol to 40 parts.

It was also demonstrated by Wright et al. that the rate of the overall reaction is basically limited by the time required for separation of the glycerol by gravity. Continuous centrifugal separation at 65° C. with a dwell time of about 5 minutes yielded a rather good result of approx. 85% of the theoretical value. Bradshaw's and Meuly's allegation that less alcohol is required in stepwise addition and glycerol removal was confirmed for methanolysis, however not for ethanolysis inasmuch as this method results in gelling.

Particularly if sodium and potassium compounds are used as catalysts, various problems are encountered in converting the triglycerides with methanol and ethanol. The catalyst which is distributed to both phases must be removed after the reaction is completed. Separation of the two phases following the reaction develops at such a low rate that large reaction volumes become necessary. In the monoester very fine glycerol droplets remain suspended and have to be washed out with water. Depending on the further use of the glycerol it is necessary to remove the dissolved catalyst. The required separation of the emulsion formed in the reaction is extremely tedious. It is considered an additional problem that the reaction at times does not immediately start up.

Owing to the described drawbacks, the above method is frequently not well suited for producing fatty acid esters under practical conditions. It is an object of the invention to provide a method for producing fatty acid esters from fatty acid triglycerides, which can be carried out simply and economically and furnishes maximum yield of the desired reaction product. The method should moreover permit for a continuous reaction process at minimum possible reaction volumes.

This object is attained by the method according to claim 1. Further embodiments result from the dependent claims.

It was surprisingly found that separation of the glycerol from the reaction mixture may be accelerated considerably by extracting the formed fatty acid ester with a near-critical extractant from the reaction mixture. Thereby the reaction rate is slowed down only insignificantly. When a liquid flow of the extractant is made to pass through the reaction mixture, phase separation is accelerated and concurrently the ensuing fatty acid ester is removed from the reaction mixture. As the obtained fatty acid esters are far more easily soluble in the extractant than triglycerides and partial glycerides, a pure product is obtained immediately under suitable conditions. Accelerating the phase separation, which constitutes the critical factor in the transesterification reaction, succeeds independent from whether the reaction is accelerated by means of homogeneous or heterogeneous catalysts. In either case, emulsions are formed which hitherto required considerable expenses for their separation.

Basically any fatty acid triglycerides may be used as starting materials for the method of the present invention. In a particularly preferred manner animal or vegetable fats or oils are used as starting materials, particularly those having 10 to 22 carbon atoms and in particular 12 to 18 carbon atoms in the fatty acid radical. As examples for vegetable starting materials, soybean oil, rape-seed oil, sunflower oil, peanut oil, cotton oil, palm oil, linseed oil, castor oil, beet oil and olive oil can be named.

The method of the invention is particularly well suited for the transesterification of fatty acid triglycerides with a monovalent low-molecular weight alcohol comprising 1 to 6 carbon atoms. Particularly preferred are alcohols comprising 1 to 4 carbon atoms and in particular methanol or ethanol. The transesterification reaction may basically take place in accordance with prior art methods. Transesterification suitably takes place at a temperature between 20 and 100° C., preferably at 30 to 80° C. and in particular at a temperature between 50 and 75° C.

Reaction of the starting materials with the monovalent low-molecular weight alcohol preferably takes place at a pressure between ambient pressure and the vapour pressure of the utilized alcohol.

Transesterification may take place in the presence of a homogeneous catalyst as well as in the presence of a heterogeneous catalyst. A particularly suitable homogeneous catalyst is an alkali. For example, all the alkylates already known in the prior art as catalysts for this reaction may be employed. By way of example the sodium or potassium alcoholates of the respective monovalent alcohol used for transesterification can be named. Sodium hydride is also suitable.

Heterogeneous catalysts have an advantage over the homogeneous catalysts in that they can more easily be separated from the reaction mixture. The framework of the invention also included a search for suitable catalysts. Herein it was found that acidic or alkaline ion exchanger resins and in particular strongly alkaline ion exchanger resins are well suited as catalysts in the transesterification of fatty acid triglycerides with monovalent alcohols. It was found that Amberlite® IRA900CI (Rohm & Haas, Darmstadt) is particularly well suited for this purpose, which prior to its use is transferred from the chloride form into the hydroxide form. This can e.g. be achieved by ion exchange with the aid of 4% soda solution and sodium hydroxide solution. Following drying by means of water-free methanol one obtains a strongly alkaline ion exchanger on a synthetic resin basis (polystyrene). As a rule, the catalyst thus obtained resulted in about 80% of the theoretical yield after a 30-minute reaction.

In accordance with the present invention, a so-called low pressure gas is used as the extractant. The term low pressure gas in this context designates a gas having a reduced temperature at 20° C. of about 0.7, preferably of equal to or greater than 0.7. Examples for such low pressure gases are carbon dioxide, propane, butane, dimethyl ether, ethyl acetate etc. Mixtures of at least two of these compositions may also be employed. The method of the invention is carried out such that the extractant is dissolved in near-critical state in the reaction mixture. The desired density of the extractant is adjusted by suitably selecting temperature and pressure. The density of the extractant suitably is at least equal to the critical density. The temperature at which extraction is carried out is between 0 and 200° C., preferably between 30 and 100° C. Preferred extractants are carbon dioxide, propane, butane or dimethyl ether. Propane, butane and dimethyl ether are particularly preferred.

It is suitable to start extraction of the formed fatty acid ester when at least 80% and in particular 80–95% of the charged fatty acid triglyceride has been reacted.

A particularly preferred embodiment of carrying out the method according to the present invention consists of feeding the emulsion to be separated, which has formed in the course of the reaction, into an extraction column, preferably into the middle portion of a countercurrent extraction column, and bringing it into countercurrent contact with the near-critical extractant. The extractant passing from below in an upward direction through the column preferably dissolves the alkyl esters which have the highest solubility among the compounds present in the reaction mixture. The undissolved portions of the charged material flow downwards in the column. Hereby the reaction mixture becomes increasingly depleted in alkyl esters, until eventually in the bottom of the counter current column a product is obtained which consists of glycerol still having slight impurities in the form of partial glycerides and triglycerides dissolved within it. If this alcoholysis is carried out with the aid of homogeneous catalysts, then the latter ones are also separated out together with the bottom product. Heterogeneous catalyst is suitably already separated out prior transferring the reaction mixture into the countercurrent extraction column.

The extract exiting from the top of the extraction column is suitably supplied to another column wherein the density of the extractant is reduced by temperature increase and/or pressure reduction to such an extent that the extracted fatty acid esters separate out quantitatively. In a particularly advantageous manner, complete separation of extractant and extract can be performed through rectification of the top product of the extraction column. Rectification is preferably carried out at a pressure which is only slightly lower than the pressure in the extraction column. It is moreover favourable to pump back part of the fatty acid esters, which are obtained with high purity at the bottom of the rectifying column, to the top of the extraction column.

The bottom product of the extraction column contains the produced glycerol and generally contains negligible impurities represented by partial glycerides and unreacted triglycerides. In the case of homogeneous catalysis, the bottom product contains the catalyst which may be removed in a further process step. This may be effected e.g. by distillation.

In the case of heterogeneous catalysis one obtains glycerol which is sufficiently pure to be immediately supplied to further use.

The method shall in the following be explained in more detail by referring to a drawing. FIG. 1 is a schematic representation of a device for carrying out the method of the present invention.

The device includes reactor B in which the reaction of the starting material—i.e. fatty acid triglyceride—with the alcohol takes place. Alcohol and triglyceride are pumped into the reaction vessel 8 via an inline mixer A. In the case of homogeneous catalysis the catalyst is suitably admixed to the alcohol beforehand. The heterogeneous catalyst is preferably filled into the reactor. The reaction mixture slowly flows through the reaction vessel. The dimensions of the reaction vessel are suitably selected such that the dwell time of the reaction mixture in the reaction vessel is sufficient for obtaining, at a temperature in the range from 20 to 100° C., a conversion of at least 80% and in particular between 80 and 90% of the theoretical rate. The reaction mixture exiting from the reactor B essentially consists of glycerol and fatty acid ester. It is pumped to the middle portion of an extractor C.

The pressure in the extractor C is higher than the vapour pressure of the extractant employed in the method of the present invention. The temperature in the extractor C is in the range from 20 to 200° C. The extractant is supplied to the bottom of extractor C and flows through the extractor from below in an upward direction in countercurrent with the reaction mixture. In the process, fatty acid ester is gradually dissolved from the reaction mixture, and the emulsion breaks up.

In the case of heterogeneous catalysis, the portion of extractor C below the port for the reaction mixture is filled with the (pelleted) catalyst. In this way practically 100% of the charged triglycerides can be converted by secondary reaction.

At the top of the extractor the extractant loaded with fatty acid ester exits from the extractor and is in the expansion valve R expanded to the pressure prevailing in the rectifying column D. After passing through heat exchanger 1 the loaded extractant is fed into the middle portion of rectifying column D. The solvent, consisting of excess alcohol and the extractant, is quantitatively separated from the extracted substances by rectification under pressure. As the bottom product of the rectifying column, solvent-free fatty acid ester is withdrawn.

The vaporous mixture of alcohol and extractant exiting from the rectifying column is cooled down in the heat exchanger 2 to such an extent that the alcohol starts to condensate out.

In the condenser E, alcohol and extractant are separated from each other by rectification at constant pressure. At the bottom of column E the obtained alcohol is withdrawn and pumped back into the inline mixer A located at the beginning of the process. The extractant exiting from column E at the top is further cooled down in the heat exchanger 3 and brought into the liquid state. The extractant condensed in the condenser F is pumped back to the bottom of the extractor C.

The embodiment represented by referring to the drawing constitutes a particularly effective mode for carrying out the method of the invention. The invention shall be explained in further detail by the following examples. Percentages indicate percent by weight.

EXAMPLE 1

200 g of fat from slaughtered animals and 1.2 times the theoretically required quantity of methanol were introduced into a stainless steel reaction autoclave. This was followed by heating to 75° C. and adding 2 g of sodium methylate as the catalyst. After vigorously stirring at ambient pressure for a period of 2.5 minutes, samples were taken from the reaction mixture and analyzed. Approx. 94% of the initial quantity of fat had been converted to methyl ester. Following interruption of the stirring process, liquid propane was conducted at a pressure of 35 bar through the reaction mixture. After exiting from the autoclave, the propane was expanded and the extract dissolved in the propane was collected in a sampling finger. The extract, minus propane still present at a low concentration, contained 87% (wt.) methyl ester and 10% (wt.) methanol. The balance was composed of triglycerides, partial glycerides and some glycerol.

EXAMPLE 2

200 g of beet oil and 1.5 times that quantity of methanol were filled into an autoclave having a capacity of 1 l. This was followed by heating to 65° C. and adding 2 g of sodium methylate. At ambient pressure vigorous stirring was performed for 5 minutes. After termination of the stirring process, samples were taken from the reaction mixture present in the form of an emulsion and analyzed. Approx. 91% of the starting product had been converted into methyl ester. Subsequently dimethyl ether was made to flow at a pressure of 30 bar through the autoclave from below in an upward direction. Upon exiting from the autoclave the dimethyl ether was expanded to ambient pressure. Hereby the extract was caused to settle and was collected in a cold finger. The extract contained about 60% methyl ester and 35% methanol minus small dimethyl ether residues. The balance was composed of triglycerides, partial glycerides and some glycerol.

EXAMPLE 3

200 g of oil from beets and 150 g of solid, alkaline catalyst Amberlite® IRA 900 were filled into an autoclave having a capacity of 1 l. Following heating to 68° C., methanol was added until boiling pressure was reached. For about 30 minutes the autoclave was shaken carefully and subsequently the catalyst was filtered from the reaction mixture. Analysis showed that 80% of the charged beet oil had been reacted into methyl ester.

EXAMPLE 4

200 g of refined coconut fat and 200 g of the alkaline catalyst Amberlite® IRA 900 were filled into an autoclave having a capacity of 1 l. After heating to 71° C., methanol was pumped in until boiling pressure was reached (approx. 1.05 atm.). After 2 hours the extraction mixture was filtered off, and the oil phase was analyzed following separation of the glycerol phase. The oil phase had the following composition: methyl ester 92.3% (wt.); diglyceride 6.6% (wt.); lycerol 1.1% (wt.).

What is claimed is:

1. A method for producing fatty acid esters comprising transesterification of fatty acid triglyceride with a monovalent alcohol of 1 to 6 carbon atoms in the presence of a homogeneous or heterogeneous catalyst in a reaction mixture, wherein said fatty acid esters are removed from said reaction mixture by extraction using a near-critical extractant, except for carbon dioxide under supercritical conditions.

2. The method according to claim 1 wherein said extractant is a gas having a reduced temperature at 20° C. of about 0.7.

3. The method according to claim 1 wherein said extractant is a gas having a reduced temperature at 20° C. of greater than about 0.7.

4. The method according to any one of claims 1 to 3 wherein said extractant is selected from the group consisting of carbon dioxide, propane, butane, dimethyl ether, ethyl acetate and a mixture of at least two of the foregoing.

5. The method according to claim 4 wherein said extractant is employed at a density which is at least equal to the critical density and at a temperature between about 0° C. and about 200° C.

6. The method according to claim 5 wherein said temperature is between about 30° C. and about 100° C.

7. The method according to claim 5 wherein propane or butane or dimethyl ether is employed as the extractant.

8. The method according to claim 1 wherein said monovalent alcohol has 1 to 4 carbon atoms.

9. The method according to claim 2 wherein said monovalent alcohol is methanol or ethanol.

10. The method according to claim 1 wherein said fatty acid triglyceride is selected from the group consisting of animal fats, animal oils, vegetable fats and vegetable oils.

11. The method of claim 10 wherein said fatty acid triglyceride has about 10 to about 22 carbon atoms in the fatty acid radical.

12. The method of claim 11 wherein said fatty acid triglyceride has about 12 to about 18 carbon atoms in the fatty acid radical.

13. The method according to claim 1 wherein an ion exchange resin is employed as the heterogeneous catalyst.

14. The method according to claim 13 wherein said ion exchange resin is a strongly alkaline ion exchange resin.

15. The method according to claim 1 wherein an alkali is employed as the homogeneous catalyst.

16. The method according to claim 1 wherein transesterification takes place at a temperature of about 20° C. to about 100° C.

17. The method according to claim 16 wherein transesterification takes place at a temperature of about 30° C. to about 80° C.

18. The method according to claim 17 wherein transesterification takes place at about 50° C. to about 75° C.

19. The method according to claim 1 wherein transesterification takes place at a pressure between ambient pressure and the vapor pressure of the monovalent alcohol.

20. The method according to claim 1 wherein said extraction is started after at least about 80% of the employed fatty acid triglyceride is converted to fatty acid ester.

21. The method according to claim 20 wherein extraction is started after about 80 to about 95% of the employed fatty acid triglyceride is converted to fatty acid ester.

22. The method according to claim 4 wherein extraction takes place in a countercurrent column to which the extractant is supplied in a lower region thereof and to which the reaction mixture to be extracted, comprising said fatty acid ester, is supplied to a middle region of the countercurrent column, and the extractant enriched with fatty acid ester and said monovalent alcohol is withdrawn at the top of the column, and glycerol substantially freed from fatty acid ester is withdrawn at the bottom of the column.

23. The method according to claim 22 wherein the extractant enriched with fatty acid ester and monovalent alcohol is freed from fatty acid ester in a rectifying column by reduced pressure, increased temperature, or the combination of reduced pressure and increased temperature, and fatty acid ester is withdrawn at the bottom and extractant enriched with monovalent alcohol is withdrawn at the top of the rectifying column.

24. The method according to claim 23 wherein the monovalent alcohol is separated from the extractant in a condenser.

25. The method according to claim 24 wherein the separated monovalent alcohol is supplied to said reaction mixture for further transesterification of said fatty acid triglyceride.

26. The method according to claim 24 wherein the extractant freed from alcohol is condensed in a condenser.

27. The method according to claim 26 wherein the extractant freed from alcohol and condensed in a condenser is recycled to the extraction column.

\* \* \* \* \*